(12) United States Patent
McGregor

(10) Patent No.: US 7,449,448 B2
(45) Date of Patent: Nov. 11, 2008

(54) COMPOSITION AND USES THEREFOR FOR COMBATING HANGOVERS

(75) Inventor: Neil Roland McGregor, Eleebana (AU)

(73) Assignee: Penam Investments Pty. Ltd., New South Wales (AU)

( * ) Notice: Subject to any disclaimer, the term of this patent is extended or adjusted under 35 U.S.C. 154(b) by 406 days.

(21) Appl. No.: 10/483,393

(22) PCT Filed: Jul. 5, 2002

(86) PCT No.: PCT/AU02/00890

§ 371 (c)(1),
(2), (4) Date: Jun. 28, 2004

(87) PCT Pub. No.: WO03/006073

PCT Pub. Date: Jan. 23, 2003

(65) Prior Publication Data

US 2004/0248819 A1    Dec. 9, 2004

(30) Foreign Application Priority Data

Jul. 10, 2001    (AU) .................................. PR6261

(51) Int. Cl.
*A01N 43/04*    (2006.01)
*A61K 31/70*    (2006.01)
*A61K 31/715*    (2006.01)

(52) U.S. Cl. .............................. 514/23; 514/53; 514/54

(58) Field of Classification Search .................... 514/23, 514/53, 54

See application file for complete search history.

(56) References Cited

U.S. PATENT DOCUMENTS 4,496,548 A * 1/1985 Moldowan et al. ............ 514/27

FOREIGN PATENT DOCUMENTS

| EP | 0 185117 | 12/1984 |
| FR | 2 748 935 | 11/1997 |
| GB | 2 308 810 A | 7/1997 |
| GB | 2308810 | * 9/1997 |
| WO | WO 99/27801 | 6/1999 |

OTHER PUBLICATIONS

Agent and Method for Reducing Alcoholic Drunkenness, Preventing and Eliminating Alcohol Intoxication and Hangover Syndrome C2001-053737; Dec. 20, 2000; M. Yasnikov DN, et al.
Derwent Abstract Accession No. 2001-180433/18, Class B05, RU 2160589-CI (Biofizika Prodn Centre Sci Prodn Assoc.).
Derwent Abstract Accesion No. 98-167658/15. Class B05 (B03), RU 2086237-CI (Nemirovskii O N).

* cited by examiner

*Primary Examiner*—Shaojia Anna Jiang
*Assistant Examiner*—Traviss C McIntosh, III
(74) *Attorney, Agent, or Firm*—Sughrue Mion, PLLC

(57) ABSTRACT

The present invention relates generally to a composition for use in the prophylaxis and/or treatment of one or more symptoms caused or exacerbated by consumption of alcohol which composition comprises: (1) fructose and (2) fructose-containing oligosaccharide.

9 Claims, No Drawings

COMPOSITION AND USES THEREFOR FOR COMBATING HANGOVERS

This is a National Stage entry of Application No. PCT/AU02/00890 filed Jul. 5, 2002; the disclosure of which is incorporated herein by reference.

FIELD OF THE INVENTION

The present invention relates generally to a composition for use in the prophylaxis and/or treatment of one or more symptoms caused or exacerbated by consumption of a toxic compound such as ethanol.

BACKGROUND OF THE INVENTION

Bibliographic details of the publications referred to by author in this specification are collected at the end of the description.

Reference to any prior art, in this specification is not, and should not be taken as an acknowledgment or any form of suggestion that this prior art is common general knowledge or forms a part of the common general knowledge in Australia or any other country.

The alcohol hangover is characterised by headache, tremulousness, nausea, diarrhoea, and fatigue combined with decreased occupational, cognitive, or visual-spatial skill performance. The symptoms of hangover seem to be caused by dehydration, hormonal alterations, deregulated cytokine pathways, and toxic effects of ethanol and its related bi-products, such as acetaldehyde. Physiological characteristics include increased cardiac work with normal peripheral resistance, diffuse slowing on electroencephalography, and increased levels of antidiuretic hormone.

Alcohol (ethanol) abuse and the resultant hangover are a substantial cost to the community. The recent review (Wiese et al, 2000) suggested that in the United States, related absenteeism and poor job performance cost $148 billion annually (average annual cost per working adult, $2000). Although hangover is associated with alcoholism, most of its cost is incurred by the light-to-moderate drinker. Subjects with hangover may pose substantial risk to themselves and others despite having a normal blood alcohol level. In Australia most motor traffic accidents are alcohol related and therefore represent a substantial problem for policing, legal, insurance and health resources. Interestingly no evidence suggests that alleviation of hangover symptoms leads to increased alcohol consumption (Wiese et al, 2000). Therefore, the development of an effective treatment is warranted, particularly a therapy which improves the cognitive and visual-spatial performance which it turn could reduce absenteeism and improve job performance.

Ethanol is metabolised to acetaldehyde by the enzyme alcohol dehydrogenase and acetaldehyde is metablised to acetate by the enzyme acetaldehyde dehydrogenase. These reactions occur predominantly in the liver but can also occur in other tissues. Ethanol and its related metabolic bi-products have many diverse influences on metabolism which include inhibition of insulin action, alteration of glycolytic enzymes and induction of the formation of oxygen radicals. These basic biochemical reactions result in a significant disturbance of neuronal and endocrine activity such as hypothalamic pituitary adrenal axis activity and catecholamine production.

In the work leading up to the present invention the instant inventor has developed a composition to enhance the metabolism of ethanol and inhibit some of the biochemical changes associated with ethanol and its bi-products, said composition being suitable for use in the prophylaxis and/or treatment of one or more symptoms caused or exacerbated by consumption of a toxic compound such as ethanol.

SUMMARY OF THE INVENTION

Throughout this specification, unless the context requires otherwise the word "comprise", and variations such as "comprises" and "comprising", will be understood to imply the inclusion of a stated element or integer or step or group of elements or integers or steps but not the exclusion of any other elements or integer or step or group of elements or integers or steps.

In one aspect of the invention there is provided a composition comprising at least one of:
  i) fructose; and
  ii) fructose-containing oligosaccharide for use in the prophylaxis and/or treatment of one or more symptoms caused or exacerbated by consumption of a toxic compound such as ethanol.

Another aspect of the present invention provides a composition comprising at least one of:
  i) fructose; and
  ii) fructose-containing oligosaccharide;

together with
  iii) a glucose-containing oligosaccharide for use in the prophylaxis and/or treatment of one or more symptoms caused or exacerbated by consumption of a toxic compound such as ethanol.

Yet another aspect of the present invention is directed to a composition comprising at least one of:
  i) fructose; and
  ii) fructose-containing oligosaccharide;

together with at least one of:
  iii) a glucose-containing oligosaccharide; and
  iv) a branched chain amino acid for use in the prophylaxis and/or treatment of one or more symptoms caused or exacerbated by consumption of a toxic compound such as ethanol.

Even yet another aspect of the present invention a composition comprising at least one of:
  i) fructose; and
  ii) fructose-containing oligosaccharide;

together with at least one of:
  iii) a glucose-containing oligosaccharide
  iv) a branched chain amino acid; and
  v) α-lipoic acid together with a B-group vitamin for use in the prophylaxis and/or treatment of one or more symptoms caused or exacerbated by consumption of a toxic compound such as ethanol.

Even yet another aspect of the present invention a composition comprising at least one of:
  vi) fructose; and
  vii) fructose-containing oligosaccharide;

together with at least one of:
  viii) a glucose-containing oligosaccharide
  ix) a branched chain amino acid; and
  x) α-lipoic acid together with a B-group vitamin when used in the prophylaxis and/or treatment of one or more symptoms caused or exacerbated by consumption of a toxic compound such as ethanol.

Yet another related aspect of the present invention provides a method for prophylaxis and/or treatment of a subject having or likely to have one or more symptoms caused or exacerbated by consumption of a toxic compound such as ethanol, said method comprising administering to said subject an effective amount of a composition as broadly described above for a time and under conditions sufficient to alleviate or prevent one or more of said symptoms.

Yet another related aspect of the present invention provides a method for prophylaxis and/or treatment of a subject having or likely to have one or more symptoms caused or exacerbated by consumption of a toxic compound such as ethanol, said method comprising administering to said subject an effective amount of at least one of:
  i) fructose; and
  ii) fructose-containing oligosaccharide;

together with at least one of:
  iii) a glucose-containing oligosaccharide
  iv) a branched chain amino acid; and
  v) α-lipoic acid together with a B-group vitamin for a time and under conditions sufficient to alleviate or prevent one or more of said symptoms.

Still yet another aspect of the present invention provides the use of at least one of:
  i) fructose; and
  ii) fructose-containing oligosaccharide;

optionally together with at least one of:
  iii) a glucose-containing oligosaccharide
  iv) a branched chain amino acid; and
  iii) α-lipoic acid together with a B-group vitamin in the manufacture of a medicament for prophylaxis and/or treatment of a subject having or likely to have one or more symptoms caused or exacerbated by consumption of a toxic compound such as ethanol.

DETAILED DESCRIPTION OF THE INVENTION

The present invention is predicated, in part, on the development of a composition to enhance the metabolism of ethanol and inhibit some of the biochemical changes associated with ethanol and its bi-products. The novel composition of the present invention and derivatives thereof are useful for the prophylaxis and/or treatment of one or more symptoms caused or exacerbated by consumption of a toxic compound such as ethanol.

The words "alcohol" and "ethanol" are used synonymously herein and refer to alcoholic compounds, their toxic metabolites and to derivatives or analogues of these.

One aspect of the invention there is provided a composition comprising at least one of:
  i) fructose; and
  ii) fructose-containing oligosaccharide for use in the prophylaxis and/or treatment of one or more symptoms caused or exacerbated by consumption of a toxic compound such as ethanol.

Reference herein to the term "oligosaccharide" includes reference to any hydrolysable polymer of one or more type of monosaccharides, said oligosaccharide containing from about 2 to 100 or more molecules of monosaccharide. Reference to an oligosaccharide includes reference to a disaccharide and a complex oligosaccharide.

Preferably, said fructose-containing oligosaccharide is sucrose or corn syrup.

In an even yet more preferred embodiment the corn syrup is high-fructose corn syrup.

Although not limiting the present invention in any way to one particular theory or mode of action, it is proposed that the inclusion of a fructose-containing oligosaccharide increases and prolongs carbohydrate availability which enhances ethanol metabolism and reduces ethanol-induced alterations in insulin responsiveness.

Accordingly, another aspect of the present invention provides a composition comprising at least one of:
  i) fructose; and
  ii) fructose-containing oligosaccharide;

together with
  iii) a glucose-containing oligosaccharide for use in the prophylaxis and/or treatment of one or more symptoms caused or exacerbated by consumption of a toxic compound such as ethanol.

Reference herein to the term "glucose-containing oligosaccharide" is used in its broadest sense and includes functional derivatives, homologues and analogues thereof which would be well known to those skilled in the art.

Preferably, said glucose-containing oligosaccharide is dextrose or a maltodextrin.

Even more preferably, said glucose-containing oligosaccharide is a corn maltodextrin.

In a further embodiment, one or more branched chain amino acids are included in the composition of the present invention. Again, without limitation to any particular mode of action or theory, branched chain amino acids are a very good source of energy and are required for protein production which is inhibited by ethanol.

Accordingly, yet another aspect of the present invention is directed to a composition comprising at least one of:
  i) fructose; and
  ii) fructose-containing oligosaccharide;

together with at least one of:
  iii) a glucose-containing oligosaccharide; and
  iv) a branched chain amino acid for use in the prophylaxis and/or treatment of one or more symptoms caused or exacerbated by consumption of a toxic compound such as ethanol.

Reference herein to "branched chain amino acid" includes reference to derivatives, homologues, analogues and mimetics thereof which will be well known to those skilled in the art. Chemical analogues of the subject amino acids contemplated herein include, but are not limited to, modification to side chains such as amino or carboxyl groups.

Preferably, said branched chain amino acid is selected from the group comprising leucine, valine and isoleucine.

Even more preferably, said branched chain amino acid is leucine.

Components of the composition may be derived from any convenient source. For example, they may be in purified form or they maybe in the form of herbs or preferably an extract of herbs or horticultural or botanical equivalents of herbs or chemical or functional equivalents of the herb extract Ethanol metabolism is dependent on the availability of oxidised $NAD^+$ which is reduced to NADH when ethanol and acetaldehyde are oxidised. In accordance with the present invention it is proposed that the deleterious effects of ethanol in increasing oxygen radical formation and reducing the availability of $NAD^+$ may be reduced by administration of a composition containing α-lipoic acid together with a B-group vitamin.

Another embodiment of the present invention contemplates therefore a composition comprising at least one of:
   i) fructose; and
   ii) fructose-containing oligosaccharide;

together with at least one of:
   iii) a glucose-containing oligosaccharide;
   iv) a branched chain amino acid; and
   v) α-lipoic acid together with a B-group vitamin for use in the prophylaxis and/or treatment of one or more symptoms caused or exacerbated by consumption of a toxic compound such as ethanol.

Preferred B-group vitamins are selected from the group comprising pantothenate and biotin.

In another related aspect of the present invention provides a method for prophylaxis and/or treatment of a subject having or likely to have one or more symptoms caused or exacerbated by consumption of a toxic compound such as ethanol, said method comprising administering to said subject an effective amount of a composition as broadly described above for a time and under conditions sufficient to alleviate or prevent one or more of said symptoms.

Yet another related aspect of the present invention provides a method for prophylaxis and/or treatment of a subject having or likely to have one or more symptoms caused or exacerbated by consumption of a toxic compound such as ethanol, said method comprising administering to said subject an effective amount of at least one of:
   i) fructose; and
   ii) fructose-containing oligosaccharide;

optionally together with at least one of:
   iii) a glucose-containing oligosaccharide;
   iv) a branched chain amino acid; and
   v) α-lipoic acid together with a B-group vitamin for a time and under conditions sufficient to alleviate or prevent one or more of said symptoms.

Yet another aspect of the present invention provides the use of at least one of:
   i) fructose; and
   ii fructose-containing oligosaccharide;

optionally together with at least one of:
   iii) a glucose-containing oligosaccharide;
   iv) a branched chain amino acid; and
   v) α-lipoic acid together with a B-group vitamin in the manufacture of a medicament for prophylaxis and/or treatment of a subject having or likely to have one or more symptoms caused or exacerbated by consumption of a toxic compound such as ethanol.

Administration of the composition of the present invention may be by any convenient route. Oral administration is generally preferred although pharmaceutical forms of the present composition may be suitable for injectable use such as sterile aqueous solutions (where water soluble) and sterile powders for the extemporaneous preparation of sterile injectable solutions or dispersions. The composition must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof and vegetable oils. The proper fluidity can be maintained, for example, by the use of a coating such as licithin. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The compositions may be orally administered, for example, with an inert diluent or with an assimilable edible carrier, or it may be enclosed in hard or soft shell gelatin capsule, or it may be compressed into tablets, or it may be in powdered form or incorporated directly with the food of the diet. For oral therapeutic and/or prophylactic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.01 μg and about 2000 mg of active compound. Alternative amounts include between about 1.0 μg and about 1500 ng, between about 1 μg and about 1000 mg and between about 10 μg and about 500 mg.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient or ingredients are compounded for convenient and effective administration in effective amounts with a suitable pharmaceutically acceptable carrier in dosage unit form. A unit dosage form can, for example, contain the principal active compounds in amounts ranging from 0.01 µg to about 70 g/100 grams. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients. Alternatively, amounts administered may be represented in terms of amounts/kg body weight. In this case, amounts range from about 0.001 µg to about 1000 mg/kg body weight may be administered 500 mg/kg body weight or about 10.01 µg to about or above 0.1 µg to about 250 mg/kg body weight are contemplated by the present invention.

Prior to case of ethanol consumption, prophylactic administration is contemplated. Preferably, the composition is administered prior to consumption of ethanol. This could be followed by an equal dose when consumption stops. Alternatively, the composition is administered when convenient thereafter. If symptoms of hangover persist, a repeat dose and/or a larger dose may be administered. The dosage and frequency of dosing is determined by a number of factors including body weight and quantity of alcohol consumed or to be consumed.

Still more preferably, the composition is administered before, during or shortly after ethanol consumption.

The present invention is now further described with reference to the following non-limiting examples.

EXAMPLE 1

The following composition was tested in subjects:

| Compound | mg per 100 Grams |
| --- | --- |
| Corn maltodextrins | 56609.1 mg |
| Fructose | 21000 mg |
| Dextrose monohydrate | 7000 mg |
| L-Alanine | 3500 mg |
| L-Leucine | 2500 mg |
| L-Isoleucine | 2500 mg |
| L-Valine | 2500 mg |
| L-Glycine | 1000 mg |
| L-Serine | 500 mg |
| L-Methionine | 50 mg |

-continued

| Compound | mg per 100 Grams |
| --- | --- |
| L-Phenylalanine | 50 mg |
| L-Arginine | 50 mg |
| L-Tyrosine | 50 mg |
| L-Histidine | 50 mg |
| L-Aspartic acid | 50 mg |
| L-Glutamic acid | 50 mg |
| L-Asparagine | 50 mg |
| L-Proline | 50 mg |
| L-Lysine | 50 mg |
| L-Threonine | 50 mg |
| L-Cystine | 50 mg |
| Sodium phosphate | 1000 mg |
| Sodium bicarbonate | 750 mg |
| Ascorbic acid | 300 mg |
| Magnesium aspartate | 150 mg |
| Nicotinamide | 30 mg |
| d-alpha Tocopheryl acetate | 20 mg |
| Ferrous fumarate | 20 mg |
| α-Lipoic acid | 10 mg |
| Calcium Pantothenate | 5 mg |
| Riboflavine | 3 mg |
| Thiamine | 2 mg |
| Betacarotene | 750 mcg |
| Biotin | 5 mcg |
| Cholecalciferol | 5 mcg |
| Cyanocobalamin | 5 mcg |
| Flavour | |

EXAMPLE 2

A male subject aged 42 years, who is a moderate drinker, took a teaspoon of the supplement of Example 1 on the morning following the consumption of an excessive amount of alcohol and reported that within 30 minutes that he was able to start to think clearly again and that most of the symptoms of his hangover were gone. This subject usually suffers significantly from hangovers.

EXAMPLE 3

A male subject aged 42 years, who is a moderate drinker, took a teaspoon of the supplement of Example 1 prior to drinking and a teaspoon following the end of the drinking session. He stated that he was not as severely effected by alcohol during his drinking session and that the following morning he did not have a hangover. This subject usually suffers significantly from hangovers.

EXAMPLE 4

The following composition is also tested in subjects:

| Compound | mg per 100 Grams |
| --- | --- |
| Corn maltodextrins | 56609.1 mg |
| Fructose | 21000 mg |
| Dextrose monohydrate | 7000 mg |
| L-Alanine | 3500 mg |
| L-Leucine | 2500 mg |
| L-Isoleucine | 2500 mg |
| L-Valine | 2500 mg |
| L-Glycine | 1000 mg |
| L-Serine | 500 mg |
| L-Phenylalanine | 50 mg |
| L-Tyrosine | 50 mg |
| L-Histidine | 50 mg |
| L-Aspartic acid | 50 mg |

-continued

| Compound | mg per 100 Grams |
|---|---|
| L-Glutamic acid | 50 mg |
| L-Asparagine | 50 mg |
| L-Proline | 50 mg |
| L-Lysine | 50 mg |
| L-Threonine | 50 mg |
| L-Cystine | 50 mg |
| Sodium phosphate | 1000 mg |
| Sodium bicarbonate | 750 mg |
| Ascorbic acid | 300 mg |
| Magnesium aspartate | 150 mg |
| Nicotinamide | 30 mg |
| d-alpha Tocopheryl acetate | 20 mg |
| Ferrous fumarate | 20 mg |
| α-Lipoic acid | 10 mg |
| Calcium Pantothenate | 5 mg |
| Riboflavine | 3 mg |
| Thiamine | 2 mg |
| Betacarotene | 750 mcg |
| Biotin | 5 mcg |
| Cholecalciferol | 5 mcg |
| Cyanocobalamin | 5 mcg |
| Flavour | |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Wiese J G, Shlipak M G, Browner W S. The alcohol hangover. *Ann Int Med,* 132:897-902, 2000.

What is claimed is:

1. A method for the treatment of a subject having one or more symptoms caused or exacerbated by consumption of alcohol, said method comprising administering to said subject an effective amount of a composition consisting essentially of:
   a fructose;
   a fructose-containing oligosaccharide;
   a glucose-containing oligosaccharide;
   a branched chain amino acid; and
   α-lipoic acid together with a B-group vitamin
   for a time and under conditions sufficient to alleviate one or more of said symptoms.

2. The method of claim 1, wherein the fructose-containing oligo saccharide is sucrose or corn syrup.

3. The method of claim 2, wherein the corn syrup is high fructose corn syrup.

4. The method of claim 1, wherein the glucose containing oligosaccharide is dextrin or maltodextrin.

5. The method of claim 4, wherein the maltodextrin is corn maltodextrin.

6. A method of claim 1, wherein said branched chain amino acid is selected from leucine, valine and isoleucine.

7. A method according to claim 1, wherein said B-group vitamin is selected from the group comprising pantothenate and biotin.

8. A method for the treatment of a subject having one or more symptoms caused or exacerbated by consumption of alcohol, said method comprising administering to said subject an effective amount of a composition consisting essentially of:
   a fructose;
   a fructose-containing oligosaccharide;
   a glucose-containing oligosaccharide;
   a branched chain amino acid;
   α-lipoic acid together with a B-group vitamin;
   alanine, glycine, serine, phenylalanine, tyrosine, histidine, aspartic acid, glutamic acid, asparagine, proline, lysine, threonine, and cystine; and
   sodium phosphate, sodium bicarbonate, ascorbic acid, magnesium aspartate, d-α tocopheryl acetate, ferrous fumarate, betacarotene, biotin, and cholecalciferol, for a time and under conditions sufficient to alleviate one or more of said symptoms.

9. A composition consisting essentially of:
   a fructose;
   a fructose-containing oligosaccharide;
   a glucose-containing oligosaccharide;
   a branched chain amino acid;
   α-lipoic acid together with a B-group vitamin;
   alanine, glycine, serine, phenylalanine, tyrosine, histidine, aspartic acid, glutamic acid, asparagine, proline, lysine, threonine, and cystine; and
   sodium phosphate, sodium bicarbonate, ascorbic acid, magnesium aspartate, d-α tocopheryl acetate, ferrous fumarate, betacarotene, biotin, and cholecalciferol,
   for use in the treatment of a subject having or likely to have one or more symptoms caused or exacerbated by consumption of alcohol.

* * * * *